United States Patent [19]

Wilcox

[11] Patent Number: 4,981,437
[45] Date of Patent: Jan. 1, 1991

[54] METHOD AND APPARATUS FOR CONSTRUCTING DENTURES

[76] Inventor: Earl R. Wilcox, 100 Dudley Ave., Old Saybrook, Conn. 06475

[21] Appl. No.: 436,363

[22] Filed: Nov. 14, 1989

[51] Int. Cl.$^5$ .............................................. A61C 11/00
[52] U.S. Cl. ....................................... 433/55; 433/64; 433/68; 433/69
[58] Field of Search ....................... 433/54, 55, 56, 64, 433/65, 57, 68, 69, 67

[56] References Cited

U.S. PATENT DOCUMENTS

| | | | |
|---|---|---|---|
| 2,610,402 | 9/1952 | Craigo | 433/71 |
| 2,746,150 | 5/1956 | Needles | 433/71 |
| 3,406,451 | 10/1968 | Anderson | 433/56 |
| 4,504,226 | 3/1985 | Gordon | 433/65 |

*Primary Examiner*—Cary E. Stone
*Attorney, Agent, or Firm*—McCormick, Paulding & Huber

[57] ABSTRACT

A method for constructing dentures which completely accommodate a patient's mandibular movements is provided. The method includes the steps of mounting a three dimensional recording device to the patient's jaws and forming intra-oral tracings of the patient's mandibular excursions and a Gothic arch tracing of the patient's mandibular excursions. The recordings and the tracing are utilized to mount upper and lower denture bases in a dental articulator, which also forms a part of the present invention, and to calibrate the articulator to precisely duplicate the patient's mandibular movements. Teeth are mounted on the upper and lower denture bases and ground to provide dentures which completely accommodate the patient's mandibular movements.

19 Claims, 2 Drawing Sheets

METHOD AND APPARATUS FOR CONSTRUCTING DENTURES

BACKGROUND OF THE INVENTION

The present invention provides a method and apparatus for constructing dentures. More particularly, the present invention provides a method and apparatus for constructing dentures which completely accommodate a patient's mandibular excursions.

The human jaw is capable of a wide variety of movements, and each individual exhibits his or her own unique set of such movements. Consequently, one of the most difficult aspects of general dentistry is providing dentures constructed to accommodate completely the excursions of the patient's jaws. In addition to accurately determining all of the physical parameters of tooth and jaw position, the dentist must at the same time attempt to satisfy the patient's needs for fit, function and esthetics.

To construct a set of dentures which meet all of the above criteria, it is first necessary to model the movements of the patient's jaws. Intra-oral tracing devices are known which utilize moldable material and scribing pins to form three dimensional recordings of the patient's mandibular excursions along the Gothic arch, curve of Wilson and curve of Spee. However, to this point no method has been devised for using the recordings to accurately position denture bases in a conventional dental articulator or to calibrate such an articulator to precisely reproduce the patient's mandibular excursions.

U.S. Pat. No. 4,273,533 to Della Croce discloses a method for constructing dentures which utilizes intra-oral recordings of the patient's mandibular movements to calibrate an articulator; however, the articulator is of Della Croce's own design and is not of the type generally known and almost universally employed by those skilled in the art.

Accordingly, it is an object of the present invention to provide a method for constructing dentures which completely accommodate the patient's mandibular excursion.

It is a further object of the present invention to provide a method for constructing such dentures on a conventional dental articulator calibrated to precisely duplicate the patient's mandibular movements.

It is a still further object of the present invention to provide a conventional dental articulator which is calibrated to precisely duplicate a patient's mandibular excursions.

SUMMARY OF THE INVENTION

The present invention meets the above-stated objects by providing a method for constructing dentures that completely accommodate the patient's mandibular excursions. The method comprises the steps of intra-orally mounting a three dimensional recording device and forming with the device intra-oral recordings of the patient's mandibular excursions and an intra-oral Gothic arch tracing of the patient's mandibular excursions. The recordings are defined by the three dimensional movement of the patient's jaws along the Gothic arch, curve of Wilson and curve of Spee. The Gothic arch tracing establishes the patient's Gothic angle.

Once the intra-oral recordings and Gothic arch tracing have been formed they are utilized to mount upper and lower denture bases in a conventional dental articulator and to calibrate the articulator to precisely duplicate the patient's mandibular movements. After the denture bases have been mounted in the articulator and the articulator is properly calibrated, teeth are mounted on the denture bases and ground to provide dentures which completely conform to the patient's mandibular excursions.

The present invention further provides a dental articulator having adjustment means capable of reproducing the movement of a patient's condylar socket centers. The adjustment means taught by the present invention enable the articulator to be calibrated in a manner which allows the articulator to precisely duplicate a patient's mandibular excursions.

DETAILED DESCRIPTION OF THE INVENTION

Figure 1:
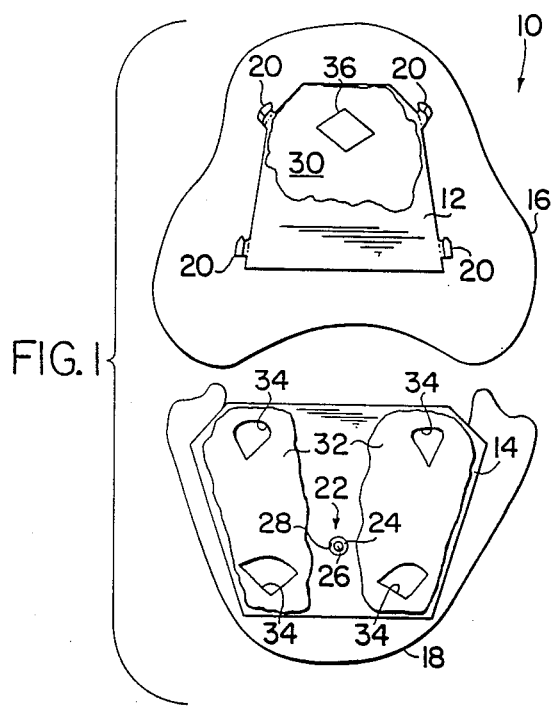
FIG. 1 is a plan view of a three dimensional recording device useful in the practice of the present invention secured on upper and lower denture bases.

An intra-oral recording device for recording a patient's mandibular excursions is shown in FIG. 1. The device, generally indicated at 10, comprises an upper tracing plate 12 and a lower tracing plate 14. FIG. 1 illustrates the upper and lower tracing plates mounted on upper and lower denture bases 16 and 18 respectively. The manner of constructing such denture bases is well known to those skilled in the art and will not be further described here. Although FIG. 1 illustrates the upper and lower tracing plates mounted on the denture bases 16, 18, those skilled in the art will recognize that the mounting of the tracing device is identical to that within a patient's mouth.

Returning now to the recording device 10, the upper tracing plate 12 is a generally trapezoidally-shaped member having four peripherally spaced pointed projections 20, 20. The projections extend toward the patient's lower jaw when the recording device is mounted intra-orally. The lower tracing plate 14 is also a generally trapezoidally-shaped member. A tracing pin 22 is mounted at the center of the anterior portion of the tracing plate 16. In the preferred embodiment of the invention, the tracing pin comprises a stylus 24 integrally formed with a threaded shaft 26. The shaft 26 is received within a threaded bore 28 formed in the lower tracing plate Vertical adjustment of the stylus 24 with respect to the tracing plate 14 is made by threading the pin into the bore and then locking the pin in the desired position with a locking nut (not shown) mounted on the shaft below the underside of the tracing plate 14.

To form a set of intra-oral recordings and a Gothic arch tracing of the patient's mandibular excursions, the lower tracing plate 14 is secured to the lower denture base so that the bearing pin 22 is located at the center of the lower denture base's stress bearing area when the patient's jaws are closed to the functional vertical of occlusion. The upper tracing plate 12 is secured to the upper denture base and the height of the tracing pin is adjusted so that there is approximately 1/16 inch clearance between the four pointed projections 20, 20 and the lower tracing plate when the patient's jaws are closed in the functional vertical of occlusion. At this point, the upper six anterior teeth 29, 29 (see FIG. 2) may be set on the upper denture base for esthetic evaluation.

Once the tracing plates are secured on their respective denture bases, a dentist or technician applies blueing compound 30 to the anterior portion of the upper tracing plate and substantially covers the lower denture plate with a quick curing tracing plastic 32, or other moldable material, taking care not to cover the tracing pin 22 with the plastic. The denture bases are then placed in the patient's mouth. (Alternatively, the blueing compound and tracing plastic may be applied to the recording device after it is placed intra-orally.)

After the recording device has been placed in the patient's mouth, the patient is instructed to move his jaws in all jaw positions. As the patient repeatedly moves his jaws in this manner, the projections 20, 20 clear away four portions of the tracing plastic to form a set of four intra-oral recordings 34, 34 of the patient's mandibular excursions. At the same time, the tracing pin 22 scratches away a portion of the blueing 30 to form a Gothic arch tracing 36 of the patient's mandibular excursions. Those skilled in the art will readily appreciate that the four recordings are defined by the three-dimensional movement of the patient's jaws along the curve of Wilson, the curve of Spee and the Gothic arch, while the Gothic arch tracing establishes the patient's Gothic angle at the center of pressure. It is important to recognize that three such intra-oral recordings define with a reasonable degree of accuracy the patient's mandibular excursions; however, a set of four such recordings provides a redundancy which eliminates residual errors that prevent the construction of dentures in complete harmony with the patient's mandibular movements.

Figure 2:
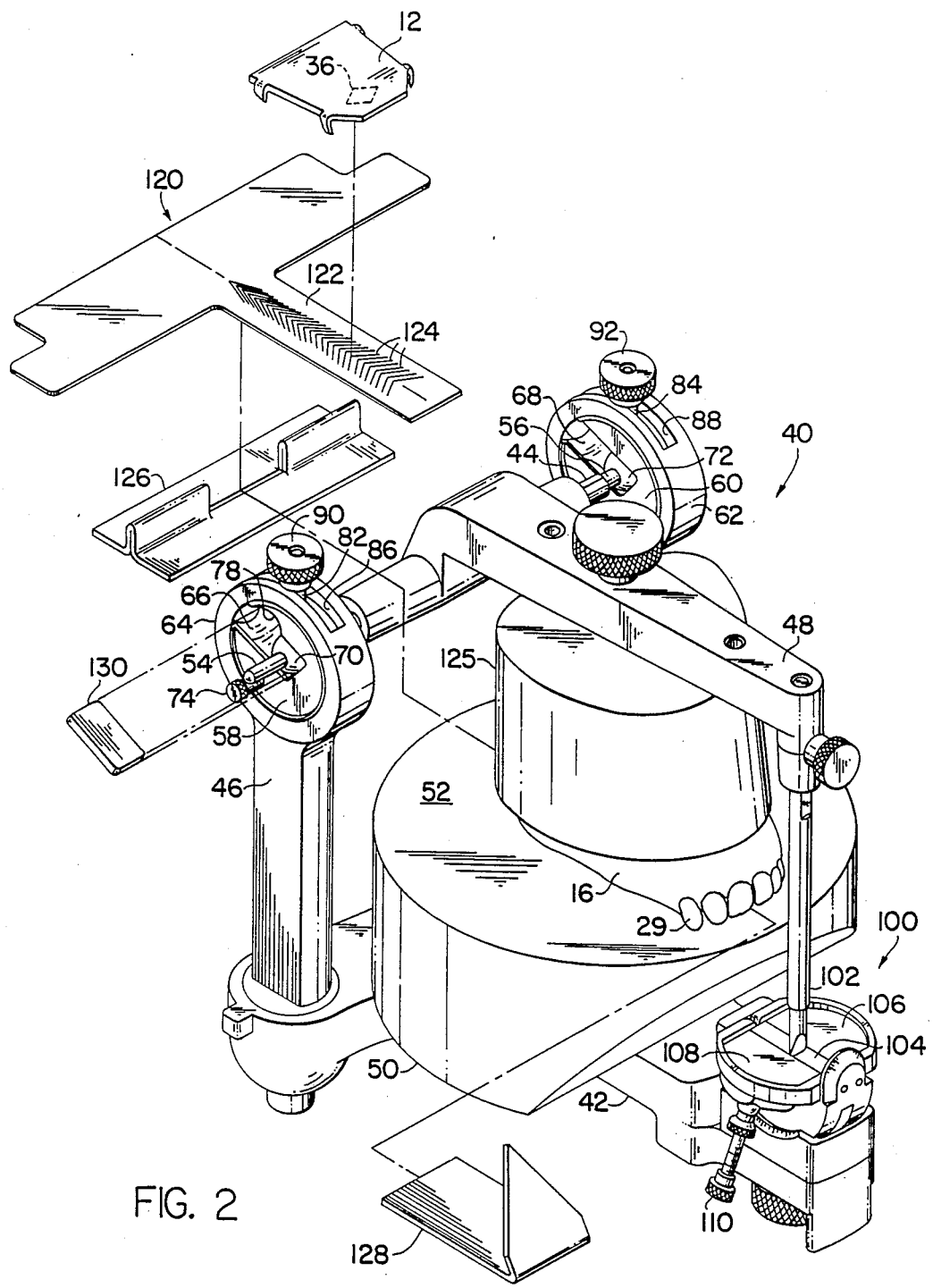
FIG. 2 is an exploded perspective view of a dental articulator with the upper denture base of FIG. 1 mounted therein.

Once the intra-oral recordings and the Gothic arch tracing have been formed with the recording device 10, they are utilized to mount the upper and lower denture bases in a conventional dental articulator and to calibrate the articulator so that the dentures constructed thereon precisely accommodate the patient's mandibular excursions. A conventional dental articulator, generally referred to as a semi-adjustable articulator, is shown in FIG. 2. Semi-adjustable articulators are well known to those skilled in the art and are almost universally employed by such persons for the construction of dentures.

An articulator of the general type shown in FIG. 2 is fully described in U.S. Pat. No. 2,237,050. Briefly, however, the articulator 40 comprises a stationary lower member 42 for receiving a lower denture (not shown) and a generally horizontal shaft 44 supported above the rearward end of the lower member on a pair of vertical posts 46, 46 (one shown). A movable upper member 48 for receiving upper denture base 16 is connected at its rearward end to the shaft 44 for angular movement about the axis of the shaft. A mounting table 50 having a horizontal mounting surface 52 is releasably mounted on the lower member 42. The mounting table supports upper denture base 16 while the denture base is positioned in the articulator.

The ends 54, 56 of the shaft 44 are supported in rotatable condylar discs 58, 60 mounted within condylar housings 62, 64 formed at the top of each post. The discs are provided with radial tracks 66, 68 journaled to receive balls 70, 72 releasably mounted on the ends of shaft. The balls are removed from the ends of the shaft by loosening set screws 74 (the set screw associated with condylar disc 60 is not shown) and moving the shaft radially outwardly along the tracks 66, 68. The articulator 40 has been modified by the present inventor to include relief portions 78 (the relief portion associated with condylar disc 60 is not shown) formed at the outward ends of the tracks. With the articulator modified in this manner, the shaft is moved radially along the track until the balls lie in the relief portions and then the balls are simply slid off the ends of the shaft.

As noted above, the condylar discs 58, 60 are rotatable within the housings 62, 64. Threaded members 82, 84 extend radially from the edges of the discs through slots 86, 88 formed in a segment of the periphery of the housings. The discs are rotatable in the housings through the angular extent of the slots 86, 88 and are locked in fixed position by tightening locking nuts 90, 92 threadably received on the threaded members 82, 84. With the shaft supported in this manner, the centers of rotation of the shaft ends 54, 56 are independently adjustable to represent the patient's condylar socket centers and reproduce their condylar movements.

The articulator 40 further comprises an incisal guide structure, generally indicated at 100, conformable to the various bite conditions of the patient. The incisal guide structure 100 includes an adjustable incisal pin 102 depending from the forward end of the upper member 48. The incisal guide structure further includes an incisal guide surface 104 pivotally mounted for anterior/posterior movement on the forward end of the articulator's lower member 42. Lateral wing members 106, 108 are pivotally mounted on opposite sides of the guide member 100 for pivotal movement about axes parallel to guide surface 104. The position of the wing members 106, 108 with respect to the guide surface 104 is adjusted by mean of adjustment screws 110, 112 (only adjustment screw 110 is shown).

To calibrate the articulator 40, the upper denture base 16, with the upper tracing plate 12 secured thereon, must be properly positioned on the upper movable member 48. This is accomplished by means of the T-shaped gauge 120 shown in FIG. 2. The center leg 122 of the gauge is marked with a series of angles 124. Each angle in the series corresponds to the Gothic angle simulated by the upper movable member at a specific; point along the anterior/posterior axis of the articulator.

The angles are generated in two segments by locking the center of rotation of one of the shaft ends at the center stop of the condylar disc in which it is supported while the opposite shaft end is left free to translate within its housing. The upper member 48 of the articulator is then moved in a horizontal arc relative to the anterior/posterior axis of the articulator to scribe the corresponding angle segment. The procedure is reversed to generate the second angle segment. Thus, each angle represents the horizontal arc of rotation produced by the upper moveable member 48 at specific points along the anterior/posterior axis of the articulator.

To properly position the upper denture base on the upper moveable member, the gauge 120 is attached to the upper tracing plate 12 so that one of the angle markings in the series 124 matches the patient's Gothic angle established by the Gothic arch tracing 36. The upper denture base is then secured to an upper mounting base 125 in the usual manner. The upper mounting base is supported on the mounting surface 52 at the Hamular notches by a posterior mounting jig 126 and at the frenum by an anterior mounting jig 128. The mounting jigs are dimensioned to mount the upper denture base in the articulator with the plane of occlusion oriented to the horizontal mounting surface 52 in accordance with the theory of Cook's plane. The final orientation of the denture base with respect to the upper member 48 is accomplished by positioning the upper mounting base and the mounting jigs on the mounting surface so that the cross leg of the gauge 120 abuts the vertical posts 46, 46 and then attaching the mounting base to the upper moveable member.

Once the upper denture base is properly positioned in the articulator, the lower denture base 18 is secured to a lower mounting base (not shown). The mounting table 50 is removed from the articulator and the lower mounting base with the lower denture base 18 secured thereto is mounted on the lower member 42 so that lower tracing plate 14 is in centric relation with upper tracing plate 12. It is important to note that for the lower denture base to be properly positioned in the articulator, the stylus 24 of the tracing pin 22 must contact the upper tracing plate 12 at the apex of the Gothic arch tracing 36 and the incisal pin 102 must contact the incisal guide surface 104.

Figure 3:
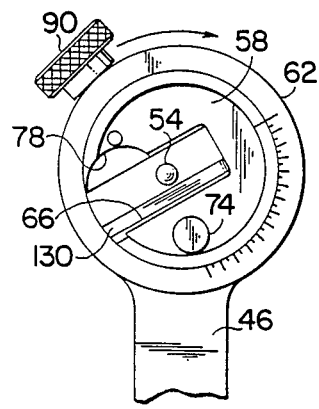
FIG. 3 is a fragmentary side elevational view of the adjustment means supporting one end of the shaft of the articulator of FIG. 2.

After the upper and lower denture bases are properly positioned in the articulator, the articulator is calibrated to reproduce the mandibular movements of the patient. Referring now to FIGS. 2 and 3, the articulator's right and left condylar angles are set by loosening set screws 74 (the set screw associated with condylar disc 60 is not shown) moving the shaft radially outwardly along the tracks 66, 68 until the balls 70, 72 lie in relief portions 78 (the relief portion associated with condylar disk 60 is not shown), and then removing the balls from the ends of the shaft. Locking nuts 90, 92 are loosened, the articulator is then moved to the protrusive position and incisal guide surface 104 is pivoted to the full negative position. A shim 130 is placed in the radial track 66, and, while the articular is firmly held in the protrusive position, condylar disc 58 is rotated until the shim 130 just contacts the shaft 44. The condylar disc 58 is fixed in this position by tightening locking nut 90. The procedure is repeated at the other end of shaft 44 and, after condylar disc 60 is locked in position the balls 70, 72 have been replaced on the ends of the shaft 44, the incisal table is pivoted upwardly to once again make contact with incisal pin 102. The articulator will now reproduce the curve of Spee recorded in the patient's intra-oral recordings.

Once the condylar angles of the articulator are set, the incisal guide structure 100 is adjusted so that the articulator will reproduce the curve of Wilson recorded in the patient's intra-oral recordings. This accomplished by pivoting lateral wing members 106, 108 by means of adjustment screws 110 (the adjustment screw associated with condylar disc 60 is not shown) so that the incisal pin 102 is in continuous contact with the incisal surface 104 and the lateral wing members 106, 108 throughout all excursions. In addition, the tracing pin 22 must follow the Gothic angle established by the patient's Gothic arch tracing, and the four pointed projections 34, 34 must be in continuous contact with the tracing plastic located at the base of the intra-oral recordings in all excursions.

With the incisal guide structure adjusted in this manner, the articulator precisely reproduces the Gothic angle, curve of Wilson and curve of Spee which define the patient's intra-oral recordings. Thus, dentures constructed on the calibrated articulator completely accommodate the patient's mandibular excursions.

While preferred embodiments have been shown and described, various modifications and substitutions may be made without departing from the spirit and scope of the invention. For example, the present invention may be used to construct an implant prosthesis which completely accommodates a patient's mandibular excursions. In such a case, the intra-oral recordings and the Gothic arch tracing are made by securing the recording device 10 on the base customarily provided to fit over the dental implants. The present invention may also be used in cases requiring a fixed bridge full mouth reconstruction. Here, the recording device 10 is attached to the cast metal or plastic copings that fit over the prepared teeth. Still further, the present invention may be used for cases where a full upper denture must be constructed against a partial lower denture. The intra-oral recordings and Gothic arch tracing are made by attaching the upper tracing plate 12 to the full upper denture base and the lower tracing plate 14 to the lower cast partial framework. In all of the above cases, the articulator mountings and calibrations are made as previously described.

Accordingly, it is to be understood that the present invention has been described by way of example and not by limitation.

I claim:

1. A method of constructing dentures which completely accommodate the mandibular excursions of a patient's jaws, said method comprising the steps of:
   (a) intra-orally mounting a three dimensional recording device;
   (b) forming with the recording device intra-oral recordings of the patient's mandibular excursions, said recordings being defined by the three-dimensional movement of the patient's jaws along the Gothic arch, the curve of Wilson and the curve of Spee;
   (c) forming with the recording device an intra-oral Gothic arch tracing of the patient's mandibular excursions, said Gothic arch tracing establishing the patient's Gothic angle;
   (d) utilizing the recordings and the Gothic arch tracing from the recording device to mount upper and lower denture bases in a conventional articulator and to calibrate the conventional dental articulator to precisely duplicate the patient's mandibular excursions; and
   (e) mounting in the calibrated articulator teeth on the upper and lower denture bases and then grinding the teeth of the denture bases to provide dentures which completely accommodate the patient's mandibular movements.

2. The method of claim 1 wherein step (a) is further characterized in that said recording device comprises an upper tracing plate intra-orally mounted on the patient's upper jaw and a lower tracing plate intra-orally mounted on the patient's lower jaw.

3. The method of claim 2 wherein step (a) is further characterized in that one of said upper and lower tracing plates has four pointed projections extending therefrom toward the other of said upper and lower tracing plates when the tracing device is mounted intra-orally, and said one of said upper and lower tracing plates has a centrally located tracing pin extending therefrom toward the other of said upper and lower tracing plates when the tracing device is mounted intra-orally, said upper and lower tracing plates intra-orally mounted so that the centrally located tracing pin contacts the other of said upper and lower tracing plates at the center of pressure when the patient's jaws are closed in the functional vertical of occlusion.

4. The method of claim 3 wherein step (a) is further characterized in that said upper tracing plate is secured on an upper denture base intra-orally mountable on the patient's upper jaw and said lower tracing plate is secured on a lower denture base intra-orally mountable on the patient's lower jaw, said upper and lower denture bases moulded to the intra-oral contours of the patient's mouth.

5. The method of claim 4 wherein step (b) is further characterized in that said recordings are formed by the steps of:
 (1) supporting the lower tracing plate on the lower denture base and the upper tracing plate on the upper denture base;
 (2) placing settable tracing plastic on one of the upper and lower tracing plates;
 (3) covering the other of the upper and lower tracing plates with blueing;
 (4) intra-orally mounting the lower denture base with the lower tracing plate supported thereon on the patient's lower jaw;
 (5) intra-orally mounting the upper denture base with the upper tracing plate mounted thereon on the patient's upper jaw, and
 (6) instructing the patient to move his jaws in all jaw positions whereby said four projections clear away four portions of the settable plastic to form said recordings and said tracing pin scratches away a portion of the blueing to form said Gothic arch tracing.

6. The method to claim 5 wherein step (d) is further characterized in that said articulator comprises adjustment means capable of reproducing the movement of the patient s condylar socket centers.

7. The method of claim 6 wherein:
 said articulator comprises a stationary lower member for receiving a lower denture, said lower member having a forward end and a rearward end, a generally horizontal shaft supported above the rearward end of said lower member by said adjustment means, said adjustment means positioned at each end of said shaft and permitting the ends of the shaft to reproduce the movement of the patient's condylar socket centers, an upper moveable member for receiving an upper denture, said upper member having a forward end and a rearward end, said upper member connected at its rearward end to the shaft for angular movement about the axis of said shaft, said upper member being movable with the shaft in a horizontal arc relative to the anterior/posterior axis of the articulator, a mounting table releasably supportable on said lower member intermediate its forward and rearward ends, said mounting table having a mounting surface defining a horizontal plane;
 and wherein step (d) includes the steps of:
 (8) providing a gauge having a series of angles marked thereon, each one of said series of angles corresponding to the horizontal arc of rotation produced by the upper moveable member of the articulator at given points on a line extending along the anterior/posterior axis of the articulator;
 (9) securing the upper denture base with the upper tracing plate supported thereon to an upper mounting base;
 (10) attaching the gauge to the upper tracing plate so that one of said series of angles matches the patient's Gothic angle established by the Gothic arch tracing formed in step (7);
 (11) supporting the mounting table on the lower member of the articulator;
 (12) attaching the upper mounting base with the upper denture base secured thereto to the upper moveable member of the articulator so that the plane of occlusion is oriented to the horizontal mounting surface of the mounting table in accordance with the theory of Cook's plane;
 (13) securing the lower denture base with the lower tracing plate supported thereon to a lower mounting base;
 (14) removing the mounting table from the lower member of the articulator and attaching the lower mounting base with the lower denture base secured thereto so that the lower tracing plate and the upper tracing plate are in centric relation.

8. The method of claim 7 wherein the adjustment means are mounted above the lower member of the articulator on a pair of posts located at the rear of the articulator and the gauge is generally T-shaped with said series of angles marked on the center leg thereof; and wherein step (12) includes the steps of:
 (A) supporting the upper mounting base at the Hamular notches with a posterior mounting jig and at the frenum with an anterior mounting jig;
 (B) positioning the upper mounting base and the mounting jigs on the horizontal surface of the mounting table so that the cross leg of the T-shaped gauge abuts the posts supporting the horizontal shaft;
 (C) attaching the upper mounting base to the upper moveable member of the articulator.

9. The method of claim 8 wherein:
 said articulator further comprises an incisal guide structure conformable to the various bite conditions of the patient, said incisal guide structure including an adjustable incisal pin depending from the forward end of the upper member toward the lower member, an incisal guide surface pivotally mounted on the forward end of said lower member for anterior/posterior movement, and lateral wing members pivotally mounted to said incisal guide member at opposite sides thereof for pivotal movement about axes parallel to said guide surface, said wing members having upper surface portions adapted to form lateral extensions of said incisal guide surface; and
 said adjustment means at each end of the shaft including a ball removably mounted on the end of the shaft, a disc having a radial track for holding the ball, the disc being rotatable in plane generally perpendicular to the shaft to set the radial track at angles corresponding to the movement of a patient's condylar socket centers, and locking means associated with the disc for locking the center of rotation of the end of the shaft in fixed position; and wherein step (d) further includes the steps of:
 (15) moving the articulator to the protrusive position;

(16) adjusting the angle of the radial track in the disc at each end of the shaft and pivoting the incisal guide surface so that the articulator precisely duplicates the curve of Spee defined in the patient's intra-oral recordings;

(17) pivoting said lateral wing member so that the articulator precisely duplicates the curve of Wilson defined in the patient's intra-oral recordings.

10. A method according to claim 1 wherein the articulator has two portions interconnected by a pivotal shaft:

and the step of utilizing the recordings to mount the upper and lower denture bases comprises mounting the denture bases in the articulator with the occlusal plane of the denture bases generally parallel to the pivotal shaft.

11. A method of constructing dentures as defined in claim 1 wherein the step of forming a set of recordings with the recording device comprises moving the patients jaws in all jaw positions with the recording device mounted intra-orally.

12. A method of constructing dentures as defined in claim 1 wherein:

the articulator has two members pivotally interconnected by a shaft, each end of the shaft being supported respectively in the slot of a rotatable bushing; and the step of utilizing the recordings comprises rotating the bushing to set the slot at an angle which corresponds to the movement of the patients condylar socket centers.

13. A method of constructing dentures as defined in claim 1 wherein:

the articulator has an upper member for holding an upper denture base and a lower member for holding a lower denture base, the lower member and the upper members being pivotally connected by a shaft; and the step of utilizing comprises placing the denture bases at a distance from the shaft axis in accordance with the Gothic arch tracing.

14. The method of claim 13 further including the step of locating the occlusal plane of the denture bases generally parallel to the shaft axis.

15. A method of constructing dentures which completely accommodate the mandibular excursions of a patient's jaws, said method comprising the steps of, (a) intra-orally mounting a three dimensional recording device to the patient's jaws;

(b) forming with the recording device intra-oral recordings of the patient's mandibular excursions, said recordings being defined by the three-dimensional movement of the patient's jaws along the Gothic arch, the curve of Wilson and the curve of Spee;

(c) forming with the recording device an intra-oral Gothic arch tracing of the patient's mandibular excursions, said Gothic arch tracing establishing the patient's Gothic angle;

(d) utilizing the recordings and the Gothic arch tracing from the recording device to mount upper and lower denture bases in a conventional articulator to calibrate the conventional dental articulator and cause the denture bases to precisely duplicate the patient's mandibular excursions; and (e) mounting in the calibrated articulator teeth on the upper and lower denture bases and then grinding the teeth of the denture bases to allow the denture bases to completely accommodate the patient's mandibular movements.

16. A method of constructing an implant prosthesis which completely accommodates the mandibular excursions of a patient's jaws, said method comprising the steps of:

(a) intra-orally mounting a three dimensional recording device to the patient's jaws;

(b) forming with the recording device intra-oral recordings of the patient's mandibular excursions, said recordings being defined by the three-dimensional movement of the patient's jaws along the Gothic arch, the curve of Wilson and the curve of Spee;

(c) forming with the recording device an intra-oral Gothic arch tracing of the patient's mandibular excursions, said Gothic arch tracing establishing the patient's Gothic angle;

(d) utilizing the recordings and the Gothic arch tracing from the recording device to mount upper and lower implant bases in a conventional articulator and to calibrate the conventional dental articulator to precisely duplicate the patient's mandibular excursions; and (e) mounting in the calibrated articulator teeth on the upper and lower implant bases and then grinding the teeth of the implant bases to provide an implant prosthesis which completely accommodate the patient's mandibular movements.

17. A method of preparing a fixed bridge full mouth reconstruction which completely accommodate the mandibular excursions of a patient's jaws, said method comprising the steps of:

(a) intra-orally mounting a three dimensional recording device to the patient's jaws;

(b) forming with the recording device intra-oral recordings of the patient's mandibular excursions, said recordings being defined by the three-dimensional movement of the patient's jaws along the Gothic arch, the curve of Wilson and the curve of Spee;

(c) forming with the recording device an intra-oral Gothic arch tracing of the patient's mandibular excursions, said Gothic arch tracing establishing the patient's Gothic angle;

(d) utilizing the recordings and the Gothic arch tracing from the recording device to mount upper and lower bridge copings in a conventional articulator and to calibrate the conventional dental articulator to precisely duplicate the patient's mandibular excursions; and (e) mounting in the calibrated articulator teeth on the upper and lower bridge copings and then grinding the teeth of the bridge copings to provide fixed bridges which completely accommodate the patient's mandibular movements.

18. A method of constructing a full upper denture against a partial lower denture which completely accommodate the mandibular excursions of a patient's jaws, said method comprising the steps of:

(a) intra-orally mounting a three dimensional recording device to the patient's jaws;

(b) forming with the recording device intra-oral recordings of the patient's mandibular excursions, said recordings being defined by the three-dimensional movement of the patient's jaws along the Gothic arch, the curve of Wilson and the curve of Spee;

(c) forming with the recording device an intra-oral Gothic arch tracing of the patient's mandibular excursions, said Gothic arch tracing establishing the patient's Gothic angle;

(d) utilizing the recordings and the Gothic arch tracing from the recording device to mount a full upper denture base and a lower cast partial framework in a conventional articulator and to calibrate the conventional dental articulator to precisely duplicate the patient's mandibular excursions; and (e) mounting in the calibrated articulator teeth on the full upper denture base and the lower cast partial framework and then grinding the teeth to provide a full upper denture and a partial lower denture which completely accommodate the patient's mandibular movements.

19. A semi-adjustable dental articulator of the type having a stationary lower member for receiving a lower denture base, a generally horizontal shaft supported above the rearward end of said lower member by adjustment means, said adjustment means positioned at each end of said shaft and including a ball removeably mounted on the end of the shaft, a disc having a radial track for holding the ball, the disc being rotatable in a plane generally perpendicular to the shaft to set the radial track at an angle corresponding to the movement of a patient's condylar socket centers and locking means associated with the disc for locking the center of rotation of the end of the shaft in fixed position, an upper moveable member for receiving an upper denture, said upper member connected to the shaft for angular movement about the axis of the shaft, wherein the improvement comprises:

relief areas formed at the outward ends of said radial tracks, said relief areas having a diameter greater than the diameter of said balls whereby said balls may be removed from the ends of the shaft when the shaft is positioned at the outward end of said tracks.

* * * * *